US006356792B1

(12) United States Patent
Errico et al.

(10) Patent No.: US 6,356,792 B1
(45) Date of Patent: Mar. 12, 2002

(54) SKULL MOUNTED ELECTRODE LEAD SECURING ASSEMBLY

(75) Inventors: Joseph P. Errico, Far Hills, NJ (US); Martin Zonenshayn, New York City, NY (US)

(73) Assignee: Electro Core Technologies, LLC, Summit, NJ (US)

( * ) Notice: Subject to any disclaimer, the term of this patent is extended or adjusted under 35 U.S.C. 154(b) by 0 days.

(21) Appl. No.: 09/489,000

(22) Filed: Jan. 20, 2000

(51) Int. Cl.[7] .............................. A61B 5/04; A61N 1/02
(52) U.S. Cl. ....................................... 607/116; 606/129
(58) Field of Search .................................. 607/115, 116, 607/139; 600/377, 378, 383, 386; 604/175; 606/108, 129, 130

(56) References Cited

U.S. PATENT DOCUMENTS

| 4,998,938 A | * | 3/1991 | Ghajar et al. |
| 5,464,446 A | * | 11/1995 | Dreessen et al. |
| 5,927,277 A | * | 7/1999 | Baudino et al. |
| 6,210,417 B1 | * | 4/2001 | Baudino et al. |

\* cited by examiner

Primary Examiner—Jeffrey R. Jastrzab
(74) Attorney, Agent, or Firm—Joseph P. Errico; Timothy J. Bartree

(57) ABSTRACT

An assembly for securing an electrode lead within a burr hole formed in a patient's skull. The assembly is provided for reliably, easily, and reversibly securing an implanted electrode lead such that the active portion of the lead which is inside the brain tissue within the skull is not subject to unwanted translations when the external portion of the lead is manipulated. The securing assembly has two separate components. The first is a bone port which seats within a preformed burr hole in the skull. The bone port is a cylindrical shaped short tube which includes a means for gripping the skull on the external periphery of the cylinder. The central axial hole of the port is designed to receive the second lead-locking portion of the assembly. The external surface of the lead-locking portion and the interior surface of the central axial hole of the port include an easily engageable coupling means, for example a bayonet locking mechanism. The lead-locking portion has a central electrode passage through which the electrode lead may slide freely in an unlocked disposition. The upper section of the lead-locking portion includes a sliding member which may be selectively manipulated between a closed and open position. The sliding member has a lateral edge which, when the member is moved into the closed position, partially occludes the electrode passage such that an electrode is secured by friction in the passage, thus preventing movement of the active implanted portion of the electrode within the skull. The external portion of the electrode, however, can be manipulated freely.

8 Claims, 3 Drawing Sheets

SKULL MOUNTED ELECTRODE LEAD SECURING ASSEMBLY

BACKGROUND OF THE INVENTION

1. Field of the Invention

This invention relates generally to a device used in the interventional treatment of neurological disorders, and more particularly to a novel electrode lead securing member which mounts to a burr hole in the patient's skull and prevents undesirable translation of the implanted lead as the external portion of the lead is manipulated during surgery.

2. Description of the Prior Art

The use of electrical stimulation of the brain for the purposes of alleviating pain and the treatment of other neurological afflictions has been utilized for a number of years, and in many instances has become the standard of care. The technique comprises the implantation of a long flexible electrical lead through a burr hole in the patient's skull, and into electrical contact with the pathological section of the patient's brain. The flexible lead comprises a plurality of long hetically wound wires encased in a elastomeric sheath. The distal end of the wire leads include electrical contacts and are placed in the brain. The proximal end of the wire leads remain external to the skull, and is coupled to an extension connector which joins the electrical wires to an electrical generator.

As is clear from the delicacy of the surgical field, it is critical to utilize robust instruments and implants which are not easily broken, and which do not lend themselves easily to unwanted movements. In particular, when an electrode lead is implanted, the position of the active tip is critical. The effects of the field generated by the electrical contacts is highly position dependent, and as a result, movement of the electrode after proper positioning can reduce or eliminate all effectiveness of the treatment. As it can be a very tedious process to find the appropriate location within the brain for the active tip, it is also critical that once the lead is situated, it should not be moved accidentally. Many of the subsequent manipulations of the external portions of the electrode leads, however, must be carried out after the active tip has been properly positioned. It is, therefore, a considerable concern that there be a means of securing the implanted portion of the electrode relative to the skull and the brain, while permitting the external portion to be moved freely. The additional feature which should be considered is that the surgeon should be able to easily manipulate any such securing device with ease, even when covered in slippery bodily fluids.

A device which is presently available in the art is illustrated in FIG. 1. This device 10 is intended to hold a flexible wire lead 12 from moving, but is not designed to seat in a hole in the patient's skull. Rather, it is designed to be secured to soft tissue (for example in the vacinity of the spinal column). The use of this device is, therefore, intended to prevent gross movement of the electrode lead 12. It is comprised of a first receiving member 14 which is cylindrical in shape. The lower portion of the cylinder forms a tapered hole 16 having an opening which is approximately the same diameter as the electrode lead 12. A second inner seating member 18 fits within the receiving member, also having an axial bore through which the electrode lead passes. The tip 20 of the seating member 18 is thin-walled, such that the channel formed therethrough may deflect inward if compressed. The second, seating member is permitted to translate within the receiving member 14 from an an open position which permits the lead 12 to freely slide through the assembly, to a closed disposition in which the tip is forced into the narrowed end 16 of the bore of the receiving member 14. In this position, the lead is friction locked in place by the compressed walls of at the tip of the seating member 18. The exterior surface of the receiving member further includes a series of through holes 20 which permit the assembly to be secured to adjacent tissue by sutures. Unfortunately, the device is very difficult to manipulate in a surgical environment as it requires manual pushing and pulling of small members which are seated within one another, and which have no defined open and closed dispositions which demonstrably indicate that the electrode lead is truly secure.

A more directly related device which is presently available in the art is illustrated in FIG. 2, and is described in U.S. Pat. No. 5,464,446. It comprises a first port member 22 which is cylindrical and seats in the burr hole formed in the patient's skull 24. The exterior lateral surface of the port includes a contoured circumferential flange portion 26 which is intended to form a seal with the inner lateral surface 28 of the burr hole. The upper portion of the port member includes an outwardly extending rim 30 which seats against the exterior surface of the skull 30 around the edge of the burr hole when the port is inserted fully in the burr hole. This upper contour is also designed to mate with a cap section 32. The central axis of the seating member 22 forms a channel through which the electrode 34 seats and can slide prior to being locked in place. The cap 32 has a pair of channels formed therein; a first 36 which extends axially along the same direction as the axial passage in the port member, and the second 38 which extends out radially along the undersurface. The cap 32 engages the upper contour (and requires a suture 40 to hold the members together) in such a way that the electrode lead is compressed and is thereby locked in place. The use of a suture to secure the electrode, even indirectly, is a considerable drawback as it is difficult to manipulate, not easily reversible, and does not provide a readily obvious means for ensuring that the lead is truly secured against movements when the external portion is manipulated during the remainder of the surgery. Also, the compression lock, as in the first example is not easily viewed as it happens under the cap member.

The objects of the present invention are, therefore, clearly to provide an electrode securing assembly which reliably, easily, reversibly, and obviously locks an electrode lead to the skull, and most importantly, prevents the unwanted movement of the implanted portion of a deep brain stimulation lead during the manipulation of the external portion after the active internal tip has been properly positioned.

More specifically, it is an object of the present invention to provide an assembly which reliably mates with a burr hole in the skull and secures an electrical lead such that it does not move within the skull, but which permits free manipulation of the portion of the electrical lead which is external to the skull.

Simultaneously, it is also an object of the present invention to provide a mechanism which is easily manipulated by the surgeon under the conditions of the surgical field.

SUMMARY OF THE INVENTION

The preceeding objects of the invention are provided by the present device which comprises a first cylindrical port member which seats into a burr hole in the skull, and a second electrode lead locking member which is bayonet locked within the port member. More particularly, the port member includes an outer surface contour which grips the inner surface of the burr hole, and a laterally extending upper lip which seats against the outer rim of the burr hole in the patient's skull. The inner surface of the port member further includes a bayonet lock receiving structure, which generally comprises a pair of diametrically opposed recesses. Corresponding laterally extending elements on te external surface of the lead locking portion are provided to fit in these recesses such that but inserting and rotating the lead locking member, it is secured within the port member. Further, the second electrode lead locking member includes a central axial channel through which the electrode is passed, and which may slide through the channel freely prior to being locked therein.

The upper portion of the lead locking member includes a sliding element which may be manipulated easily between an offset position and an occluding position. These alternate dispositions, and more particularly, the movements between them, are transverse to the axis of the member and the orientation of the electrode. Specifically, the sliding element is a disc which is seated in the upper surface of the lead locking member. The disc is initially offset relative to the hole which is the terminus of the axial channel. The disc slides along a track in the upper surface of the member into a closed position which partially blocks the hole. In this occluding position, the sliding member partially narrows the channel, and if there is an electrode lead extending therethrough, the lead is squeezed by the sliding member and thereby prevented from continued relative motion. The sliding member, or disc, may include at least one small recess into which a tool may be inserted to facilitate the translation between the open and closed positions. The track in which the sliding member translates, may further include a tab, ratchet, catch, or other structural feature by which the surgeon/user may readily recognize if the sliding element has ben fully engaged at the open or closed position.

Unlike prior devices, two of which are described above, the manipulation of the locking mechanism of the present invention is readily visible to the user, as it involves the translation of a sliding member transverse to the axial channel at the upper surface of the lead locking member. This feature may prevent additional mistakes associated with incomplete fixation of the lead in the locking mechanism.

The present device also resolves the difficulty of use which is a limitation of the prior art devices. By providing recesses in which a tool, for example a scissors, plyers, or other hand-held retractor, may engage and manipulate the mechanism, the present invention eliminates a substantial drawback to using similar prior art devices.

In addition, the reversibility of the locking mechanism is very easy to achieve, i.e. simply reversing the bias of the sliding element away from the hole or rotating and removing the lead locking member from the port member, is a substantial advance over semi-permanent securing means which require sutures to secure the assembly to the adjacent tissue, and sutures to hold a lead locking cap member to the lead receiving member.

Additional advantages ofthe present invention shall be readily understandable from the detailed description of certain preferred embodiments described more completely in the following sections, and with reference to the accompanying figures.

A BRIEF DESCRIPTION OF THE DRAWINGS

THE DETAILED DESCRIPTION OF THE PREFERRED EMBODIMENTS

While the present invention will be described more fully hereinafter with reference to the accompanying drawings, in which particular embodiments are shown, and with respect to methods of implantation, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
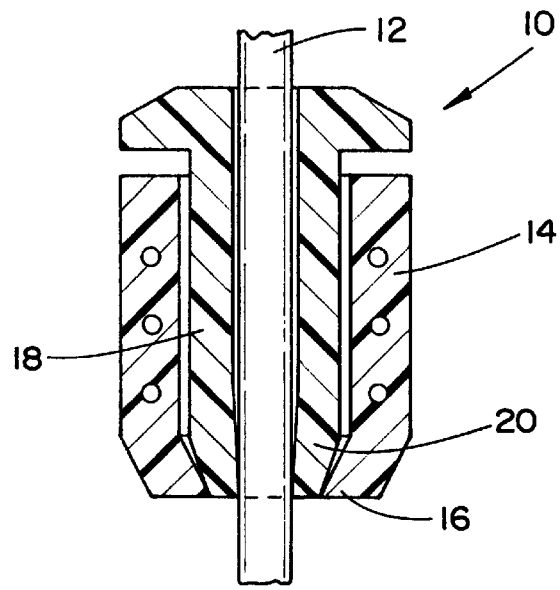
FIG. 1 shows a side cross section view of a prior art device for securing an electrical lead.
Figure 2:
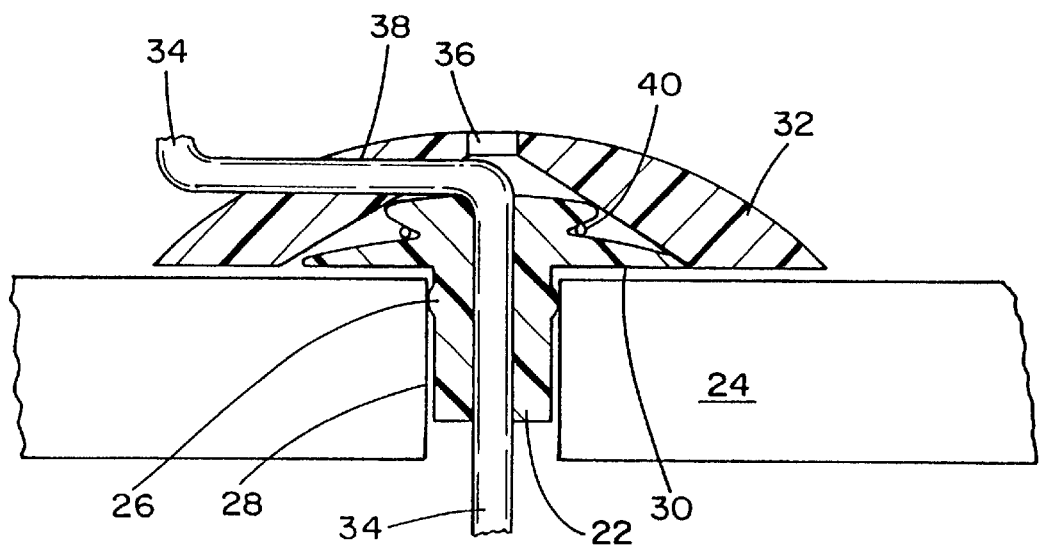
FIG. 2 shows a side perspective view of another electrode securing device of the prior art which couples to the skull.
Figure 3:
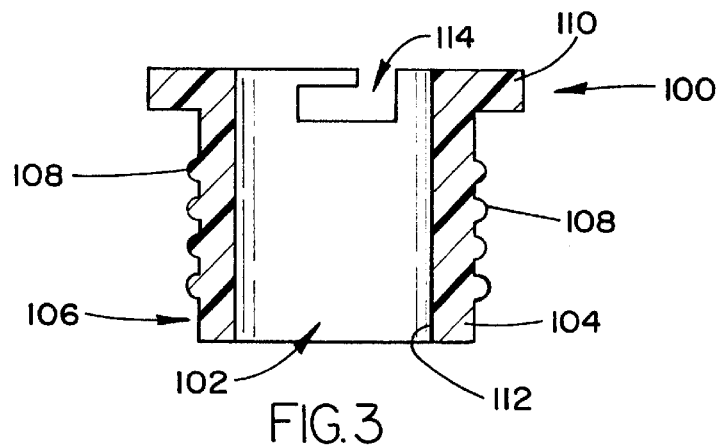
FIG. 3 shows a cross-section view of a burr hole port which are an aspect of the present invention.

Referring now to FIG. 3, the present invention comprises a cylindrical skull port member 100 which is designed to securely fit within the burr hole formed in a patient's skull,through which the surgeon implants the active tip of the electrode lead. The cylindrical port member 100 includes a central opening 102 and a round sidewall 104. The exterior surface 106 of the sidewall includes at least one circumferential rib 108, and preferably multiple ribs 108. These ribs are preferably made of an elastomeric material (for example silicone). These ribs are provided for enhanced gripping and holding of the inner surface of the burr hole in the skull. Other than these ribs, the exterior surface of the cylindrical port is largely smooth, having only a laterally extending lip 110 at the upper end. This lip 110 is provided so that as the port 100 is inserted into the burr hole, the lip 110 seats against the upper surface of the skull and prevents the port 100 from passing too deeply into the brain case.

The interior surface 112 of the port's central opening is also largely smooth, being suited to receive therethrough the lead locking element described hereinbelow with respect to FIGS. 4a, 4b, and, in combination with the port member, FIG. 5. The central opening 102 does, however, include engaging means for securing the leadlocking member therein. In the present embodiment, this engaging means comprises a bayonet lock receiving groove 114. In particular, the upper portion of the port includes a pair of opposing lateral recesses 114 (one of which is shown in FIG. 3) which extends downward from the upper surface for a short distance, and then turns laterally, forming a partial circumferential groove.

Figure 4A:
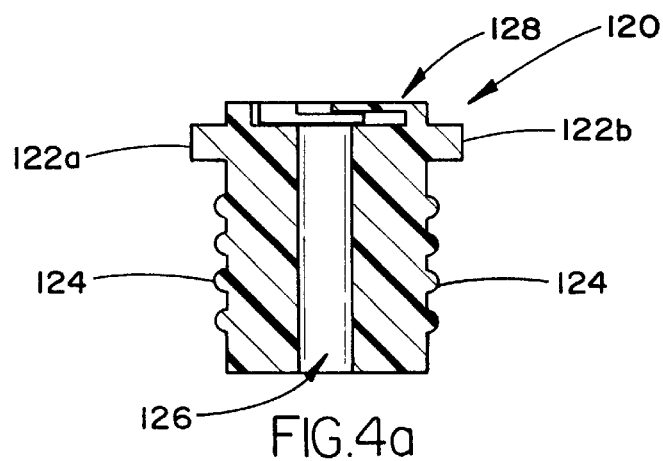
FIGS. 4a and 4b show side cross-section and top views, respectively, of the electrode lead locking portion of the present invention.

Referring now to FIG. 4a, the lead locking element 120 is provided in a side cross section view. The lead locking element 120 is generally cylindrical in shape, having a pair of laterally extending posts 122a,122b extending outwardly from the upper end of the element. These posts 122a,122b are provided to engage the grooves 114 in the upper inner surface of the port member 100. The lead locking element 120 also includes at least one (and preferably a plurality of circumferential elastomeric ribs 124. The element 120 is designed to slide into the central opening 102 of the port member 100, with the elastomeric ribs 124 of the lead locking element 120 gripping the inner surface 112 of the opening 102 in the port 100. The laterally extending posts 122a,122b are then inserted into the opposing grooves 114 in the central opening, and then rotated such that the lead locking element 120 may not translate axially relative to the port member.

The lead locking element 120 further includes an axial channel 126 through which the brain stimulation lead may be passed. The lead may initially loosely translate within the channel 126 so that the lead locking element 120 may freely slide along the lead and into the port member 100.

Figure 4B:
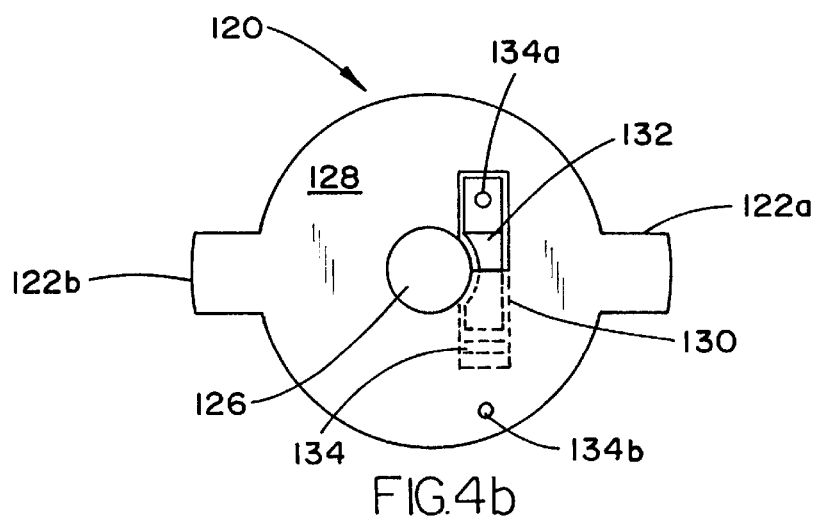

The upper surface 128 of the lead locking element 120 further includes a lead locking mechanism, which is more evidently shown in FIG. 4b, which is a top view of the element 120. More particularly, the upper surface 128 of the lead locking element includes a partially covered track 130 in which is seated a sliding element 132. The track 130 is adjacent to the upper opening of the axial channel 126. Within the track 130 is a sliding element 132 which may be selectively translated from one end of the track to the other. A portion of the sliding element is maintained within the covered portion of the track, while a portion remains free so that the user may engage it. When in the open disposition, the sliding element does not occlude the opening, however, when translated into the closed position, the sliding element partially blocks the opening. More importantly, this partial occlusion, when the stimulation lead is present in the channel, compresses the lead sufficiently to prevent any further axial movement of the lead. The track may also include ratcheting conformations 134 which indicate to the user that the sliding element has been fully translated into the closed position. This indication will provide greater security to the surgeon by indicating that the device has been fully locked.

In order to facilitate the selective manipulation of the sliding element 132, the sliding element 132 and the upper edge of the lead locking element each include tool receiving recesses 134a,134b. A scissor-like instrument (or other similar tool) may be utilized to translate the sliding element from the open to closed position (or conversely, to open the assembly by moving the sliding element from the closed to open position).

Figure 5:
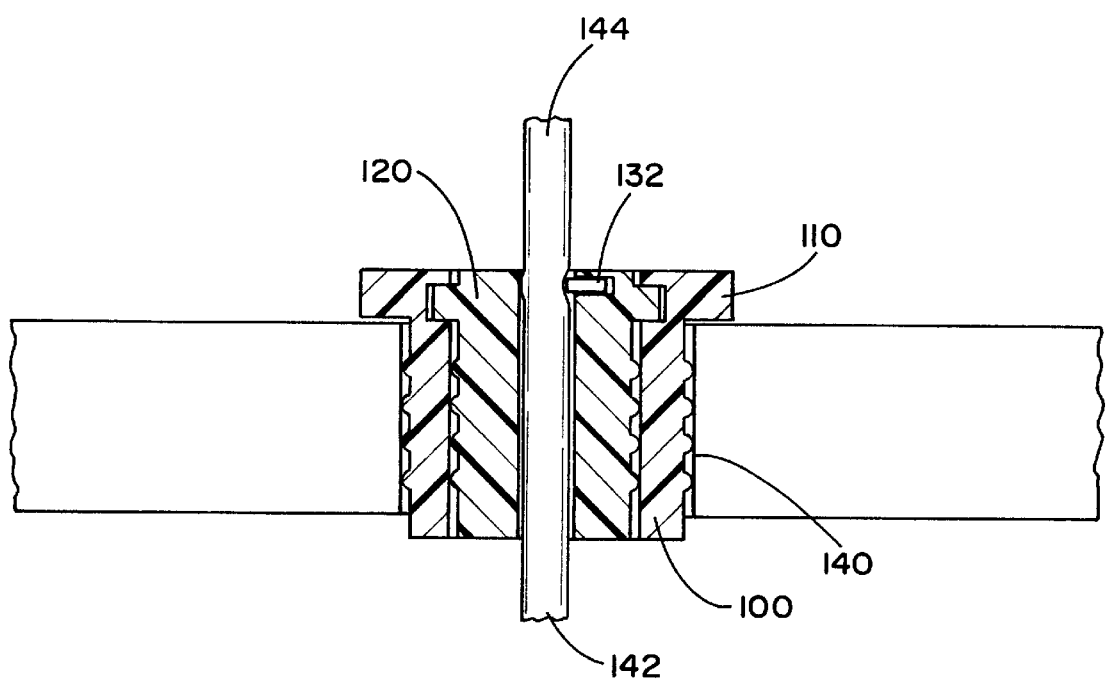
FIG. 5 shows a side cross section view of the assembly mounted in a burr hole and locking an electrode disposed therethrough.

Referring now to FIG. 5, in which a fully implanted and closed assembly is provided in a side cross section, a description of the use of the present invention is described. Preparation for the implantation of a deep brain stimulation lead begins with the exposure of a portion of the skull (usually above the crown of the head, above the motor cortex). A burr hole 140 is then formed in the skull. Fourteen millimeters is a standard burr hole diameter. The port member 100 is then installed in the burr hole, until the upper lip 110 seats against the skull surface. The exterior end of the electrode is temporarily fastened to a fixed exterior structure, for example the stereotactic surgical frame which is usually mounted by screws to the patient's skull. Once this has been prepared, a cannula is advanced into the patient's brain, often guided by computer imagery and magnetic sensors. The cannula carries a microelectrode recordation device, with which the surgeon tests to find the ideal location for the permanent implant lead. Once found, the microelectrode recording lead is removed and the active tip of the electrode 142 is advanced into the brain, to the location which was identified. Once properly located, the cannula is removed from the brain by being carefully slid up along the lead electrode lead. This process must be carried out carefully so as not to disturb the location of the active tip. Once the cannula is free of the brain, the lead is manually held fixed at the port member 100, and the exterior end of the lead is released as the cannula slides completely off the lead. Once freed, the exterior end of the electrode is advanced through the lead locking element 120, and the lead locking element is inserted into the port member 100 and rotated into a secured disposition. The stylet, which is a rigidity providing component of the electrode lead, is then removed. The limp lead is then locked in place by the surgeon who translates the sliding element 132 of the lead locking element 120 into the closed disposition. The interior portion of the lead is thereby prevented from any motion, while the exterior portion 144 of the lead is free to be manipulated as necessary for connections to a signal generator, or other electrical signal providing mechanism.

While there has been described and illustrated specific embodiments of new and novel electrode lead securing assembly for reliably and securely fixing an implanted electrode lead to the skull, it will be apparent to those skilled in the art that variations and modifications are possible without deviating from the broad spirit and principle of the present invention which shall be limited solely by the scope of the claims appended hereto.

We claim:

1. An electrode securing assembly for securing an electrode lead to a skull of a patient; comprising:

a cylindrical port element for seating in a hole formed in said skull of said patient, said port element including a central channel providing communication between an interior of said skull and an exterior of said skull, at least one engaging means formed on at least one inner surface of said central channel, and at least one exterior conformation for gripping an interior surface of an opening formed in said skull of said patient;

a lead locking element having an upper and lower portion, said lead locking element seating within the central channel of said port element, having at least one corresponding engaging means formed on the exterior surface thereof, said at least one engaging means of said port element and said at least one corresponding engaging means of said lead locking element for securing said lead locking element to said at least one engaging means of said port element;

said lead locking element further including an axial passage for receiving therethrough an electrode lead which has a portion implanted within said patient's skull and a portion remaining external to said skull, such that said electrode may initially freely slide within said passage;

said lead locking element further including a track formed in said upper portion thereof;

a sliding element, mounted in said track of said lead locking element, which may be selectively translated along said track between at least two distinct positions, at least one of which partially blocks said axial passage in said lead locking element, and at least one position which does not block said axial passage;

such that when said sliding element is translated into the axial passage blocking position, and when there is an electrode lead disposed in said passage it is prevented from further movement through the passage.

2. The electrode securing assembly as set forth in claim 1, wherein engaging means formed on at said inner surface of said port element and said corresponding engaging means formed on the exterior surface of said lead locking element comprises at least one bayonet locking tongue and groove mechanism, whereby said lead locking element may be inserted into said port element and by rotation thereof, locked therein.

3. The electrode securing assembly as set forth in claim 1, wherein said sliding element further include at least one exterior surface tool receiving recess whereby said sliding element may be selectively translated within said track of said lead locking element by applying a translational force via said tool receiving recess.

4. The electrode securing assembly as set forth in claim 1, wherein said track includes at least two separate registration ratchets which,when engaged, hold said sliding element at a specific location along the track, said registration ratchets being provided at locations such that the sliding element may be retained at open or a closed positions.

5. The electrode securing assembly as set forth in claim 1, wherein said port member has an exterior surface that includes at least one circumferential rib for enhancing the gripping of the port to the interior surface of said hole in said skull.

6. The electrode securing assembly as set forth in claim 5, wherein said at least one circumferential rib of said port member comprises an elastomeric material.

7. The electrode securing assembly as set forth in claim 1, wherein said lead locking element includes at least one circumferential ribs formed on the exterior surface which engages the interior surface of the port member, for enhancing the gripping of the lead locking element within the port member.

8. The electrode securing assembly as set forth in claim 7, wherein said at least one circumferential rib of said lead locking element comprises an elastomeric material.

* * * * *